(12) United States Patent
Hollst

(10) Patent No.: US 11,660,364 B2
(45) Date of Patent: *May 30, 2023

(54) APPARATUS FOR GENERATING AQUEOUS OZONE

(71) Applicant: CleanCore Solutions, Inc., Omaha, NE (US)

(72) Inventor: Gary Hollst, Omaha, NE (US)

(73) Assignee: CLEANCORE SOLUTIONS, INC., Omaha, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/347,364

(22) Filed: Jun. 14, 2021

(65) Prior Publication Data
US 2022/0072172 A1 Mar. 10, 2022

Related U.S. Application Data

(63) Continuation of application No. 15/976,690, filed on May 10, 2018, now Pat. No. 11,033,647.

(60) Provisional application No. 62/612,170, filed on Dec. 29, 2017.

(51) Int. Cl.
| | |
|---|---|
| *A61L 2/18* | (2006.01) |
| *A61L 2/24* | (2006.01) |
| *C01B 13/11* | (2006.01) |
| *A23N 12/00* | (2006.01) |

(52) U.S. Cl.
CPC .............. *A61L 2/183* (2013.01); *A61L 2/24* (2013.01); *C01B 13/115* (2013.01); *A23N 12/00* (2013.01); *A61L 2202/11* (2013.01); *A61L 2202/14* (2013.01); *A61L 2202/17* (2013.01); *C01B 2201/62* (2013.01); *C01B 2201/90* (2013.01)

(58) Field of Classification Search
CPC ...................................................... A61L 2/183
See application file for complete search history.

(56) References Cited

U.S. PATENT DOCUMENTS

| | | | |
|---|---|---|---|
| 2,417,932 | A | 3/1947 | Kalmar |
| 3,719,327 | A | 3/1973 | McMahan |
| 5,248,218 | A | 9/1993 | Belcher |
| 5,364,034 | A | 11/1994 | Hirahara |

(Continued)

OTHER PUBLICATIONS

International Search Report and Written Opinion dated Mar. 26, 2019 for PCT/US2018/68115.

*Primary Examiner* — Jason Y Ko
(74) *Attorney, Agent, or Firm* — HEA Law PLLC; Darrin Auito

(57) ABSTRACT

An apparatus includes a first production line configured to generate aqueous ozone with a first ozone concentration. The apparatus also includes an additional production line configured to generate aqueous ozone with an additional ozone concentration. The first production line and the additional production line include a flow switch, where fluid is configured to flow through the flow switch. The first production line and the additional production line include an ozone generator, where the ozone generator is configured to generate ozone when the fluid flows through the flow switch. The first production line and the additional production line include a fitting coupled to the flow switch and the ozone generator, where the fitting is configured to combine the generated ozone and the fluid to generate the aqueous ozone. The first production line is configured to generate aqueous ozone independently from the additional production line.

17 Claims, 13 Drawing Sheets

(56) References Cited

U.S. PATENT DOCUMENTS

| | | |
|---|---|---|
| 5,945,068 A | 8/1999 | Ferone |
| 6,006,387 A | 12/1999 | Cooper et al. |
| 6,132,629 A | 10/2000 | Boley |
| 6,153,105 A | 11/2000 | Tadlock et al. |
| 6,334,328 B1 | 1/2002 | Brill |
| 6,685,825 B1 | 2/2004 | Chang |
| 8,071,526 B2 | 12/2011 | Lynn |
| 8,075,705 B2 | 12/2011 | Lynn |
| 9,068,149 B2 | 6/2015 | Lynn |
| 9,151,528 B2 | 10/2015 | Erbs et al. |
| 9,174,845 B2 | 11/2015 | Lynn |
| 9,522,348 B2 | 12/2016 | Lynn |
| 2004/0004042 A1 | 1/2004 | Hadley et al. |
| 2004/0168989 A1 | 9/2004 | Tempest, Jr. |
| 2006/0127551 A1 | 6/2006 | Lewis |
| 2009/0142225 A1 | 6/2009 | Tornqvist |
| 2010/0021598 A1 | 1/2010 | Lynn |
| 2010/0219137 A1 | 9/2010 | Lacasse |
| 2012/0193303 A1 | 8/2012 | Hengsperger et al. |
| 2013/0193081 A1 | 8/2013 | Vasiliu et al. |
| 2013/0341285 A1 | 12/2013 | Marion |
| 2014/0027388 A1 | 1/2014 | Constant |
| 2014/0263097 A1 | 9/2014 | Lynn |
| 2016/0251243 A1 | 9/2016 | Lynn |

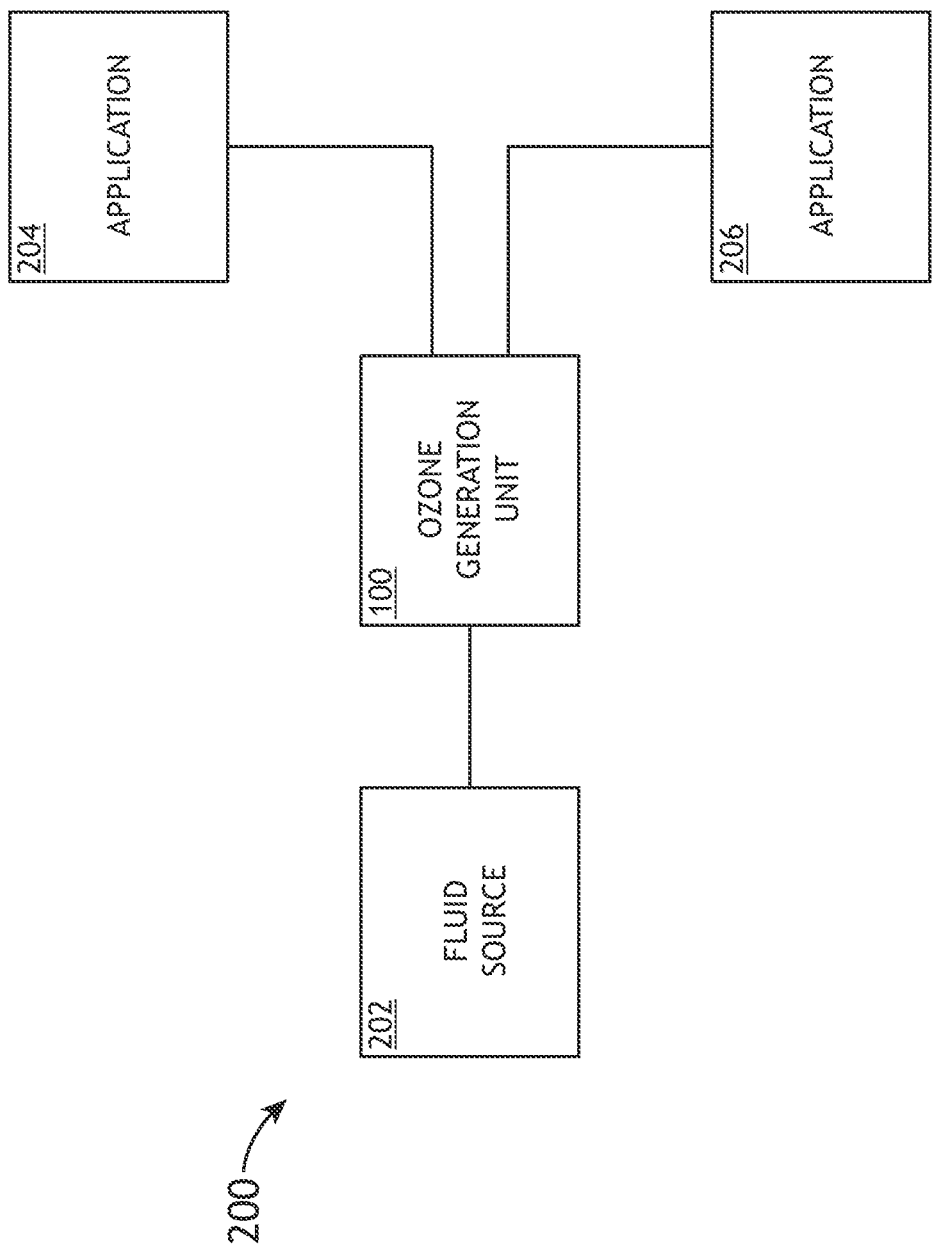

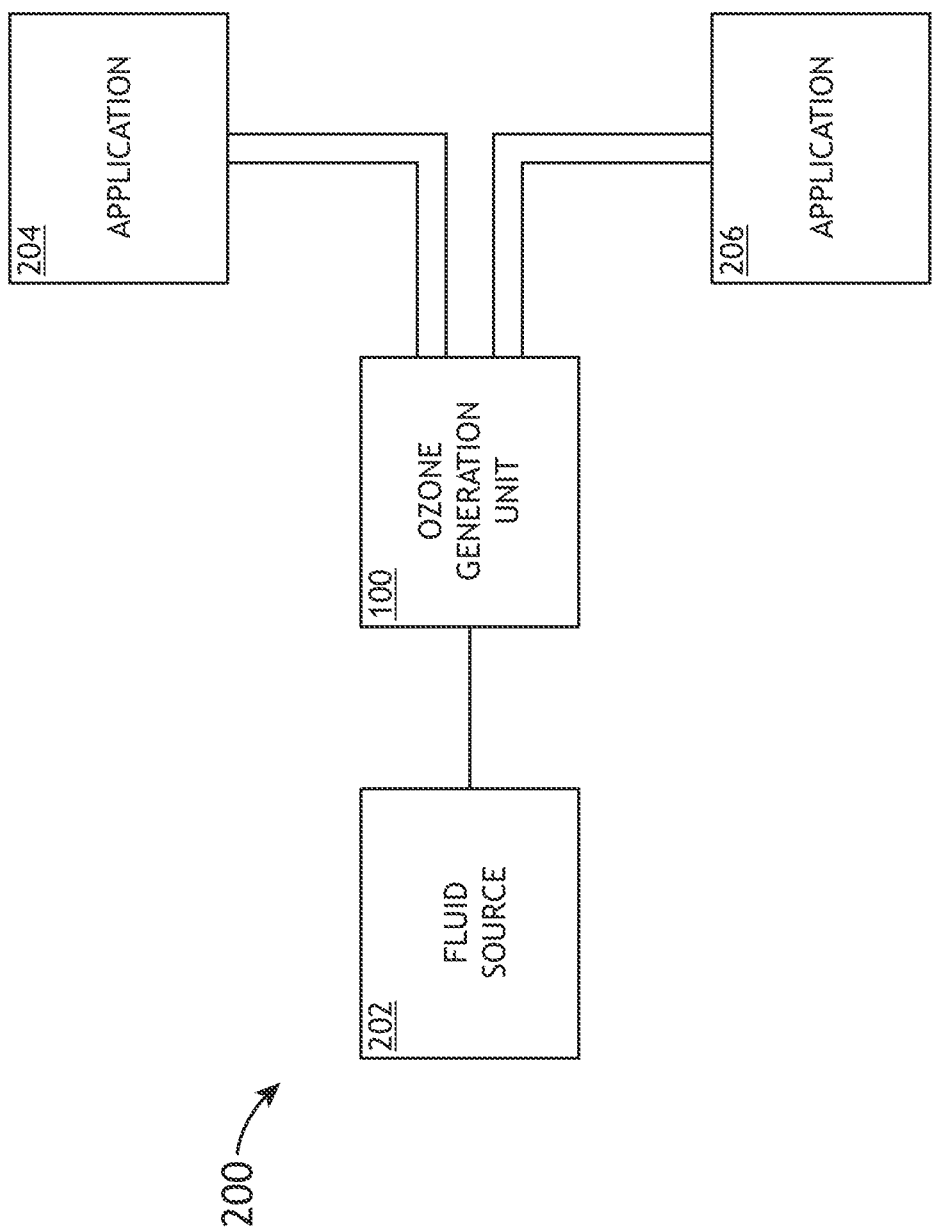

APPARATUS FOR GENERATING AQUEOUS OZONE

CROSS-REFERENCE TO RELATED APPLICATIONS

The present application constitutes a continuation application of U.S. patent application Ser. No. 15/976,690, filed on May 10, 2018, which is a non-provisional application of U.S. Provisional Patent Application Ser. No. 62/612,170, filed Dec. 29, 2017, entitled APPARATUS FOR GENERATING AQUEOUS OZONE, naming Gary Hollst as inventor, whereby each of the list applications is incorporated herein by reference in their entirety.

TECHNICAL FIELD

The present invention generally relates to applications requiring aqueous ozone and, in particular, to an apparatus for generating aqueous ozone.

BACKGROUND

In many industries (e.g., sanitation industries, food processing, or the like) and facilities (e.g., healthcare facilities, restaurants, schools, homes, commercial buildings, offices, lodging, or the like), aqueous ozone ($O_3$) is utilized in applications needing to maintain a specific level of water quality. Traditionally, the amount of aqueous ozone necessary is application-specific, with many applications requiring a particular ozone concentration, particular amount of water pressure, particular volume of water flow, or the like. For example, too high of an ozone concentration may result in off-gassing. By way of another example, too low of an ozone concentration will result in reduced levels of cleanliness and/or sanitation. Due to the specific requirements, multiple aqueous ozone production lines may be required for each application.

Alternative solutions to the use of aqueous ozone production systems generally require the use of caustic and/or dangerous chemicals. The chemicals may injure users and/or damage the environment following disposal of the chemicals. While non-chemical alternatives (e.g., oxidizers including, but not limited to, chlorine) exist, the known alternatives require extensive time when implemented as a cleansing and/or sanitizing agent.

As such, it would be desirable to provide an apparatus that addresses the shortcomings of the previous approaches listed above.

BACKGROUND

An apparatus is disclosed, in accordance with one or more embodiments of the present disclosure. In one embodiment, the apparatus includes a first production line configured to generate aqueous ozone with a first ozone concentration. In another embodiment, the apparatus includes an additional production line configured to generate aqueous ozone with an additional ozone concentration. In another embodiment, the first production line and the additional production line include a flow switch. In another embodiment, fluid is configured to flow through the flow switch. In another embodiment, the first production line and the additional production line include an ozone generator. In another embodiment, the ozone generator is configured to generate ozone when the fluid flows through the flow switch. In another embodiment, the first production line and the additional production line include a fitting coupled to the flow switch and the ozone generator. In another embodiment, the fitting is configured to combine the generated ozone and the fluid to generate the aqueous ozone. In another embodiment, the first production line is configured to generate aqueous ozone independently from the additional production line.

A system is disclosed, in accordance with one or more embodiments of the present disclosure. In one embodiment, the system includes one or more fluid sources. In another embodiment, the system includes an ozone generation unit. In another embodiment, the ozone generation unit includes a first production line configured to generate aqueous ozone with a first ozone concentration. In another embodiment, the ozone generation unit includes an additional production line configured to generate aqueous ozone with an additional ozone concentration. In another embodiment, the first production line and the additional production line include a flow switch configured to receive fluid from a fluid source of the one or more fluid sources. In another embodiment, the fluid is configured to flow through the flow switch. In another embodiment, the first production line and the additional production line include an ozone generator. In another embodiment, the ozone generator is configured to generate ozone when the fluid flows through the flow switch. In another embodiment, the first production line and the additional production line include a fitting coupled to the flow switch and the ozone generator. In another embodiment, the fitting is configured to combine the generated ozone and the fluid to generate the aqueous ozone. In another embodiment, the first production line is configured to generate aqueous ozone independently from the additional production line. In another embodiment, the system includes one or more applications configured to receive the aqueous ozone generated by the first production line and receive the aqueous ozone generated by the additional production line.

A system is disclosed, in accordance with one or more embodiments of the present disclosure. In one embodiment, the system includes one or more fluid sources. In another embodiment, the system includes an ozone generation unit. In another embodiment, the ozone generation unit includes a first production line configured to generate aqueous ozone with a first ozone concentration. In another embodiment, the ozone generation unit includes an additional production line configured to generate aqueous ozone with an additional ozone concentration. In another embodiment, the first production line and the additional production line include a flow switch configured to receive fluid from a fluid source of the one or more fluid sources. In another embodiment, the fluid is configured to flow through the flow switch. In another embodiment, the first production line and the additional production line include an ozone generator. In another embodiment, the ozone generator is configured to generate ozone when the fluid flows through the flow switch. In another embodiment, the first production line and the additional production line include a fitting coupled to the flow switch and the ozone generator. In another embodiment, the fitting is configured to combine the generated ozone and the fluid to generate the aqueous ozone. In another embodiment, the first production line is configured to generate aqueous ozone independently from the additional production line. In another embodiment, the system includes one or more programmable washing machines configured to receive the aqueous ozone generated by the first production line and receive the aqueous ozone generated by the additional production line.

BRIEF DESCRIPTION OF THE DRAWINGS

The numerous advantages of the disclosure may be better understood by those skilled in the art by reference to the accompanying figures in which:

FIG. 2B illustrates a simplified block diagram of a system including an apparatus for generating aqueous ozone, in accordance with one or more embodiments of the present disclosure;

FIG. 2C illustrates a simplified block diagram of a system including an apparatus for generating aqueous ozone, in accordance with one or more embodiments of the present disclosure;

DETAILED DESCRIPTION OF THE INVENTION

Reference will now be made in detail to the subject matter disclosed, which is illustrated in the accompanying drawings.

FIGS. 1A-3 generally illustrate an apparatus for generating aqueous ozone ($O_3$), in accordance with one or more embodiments of the present disclosure.

Embodiments of the present disclosure are directed to an apparatus for generating aqueous ozone. Embodiments of the present disclosure are also directed to a system including the apparatus for generating aqueous ozone. Embodiments of the present disclosure are also directed to providing the generated aqueous ozone to one or more applications. Embodiments of the present disclosure are also directed to a method for generating the aqueous ozone via the apparatus and providing the aqueous ozone to applications.

Figure 1A:
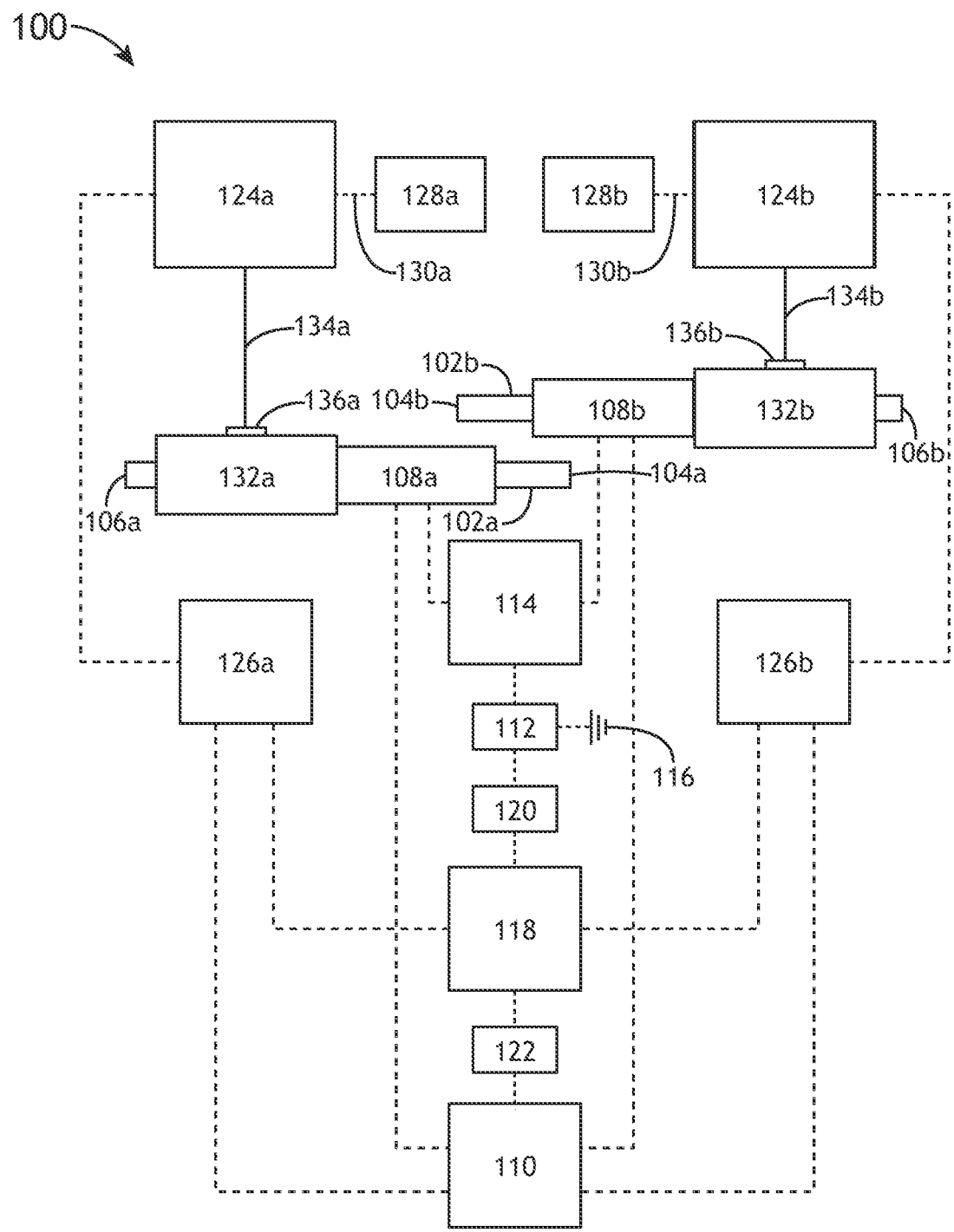
FIG. 1A illustrates a simplified block diagram of an apparatus for generating aqueous ozone, in accordance with one or more embodiments of the present disclosure.
Figure 1B:
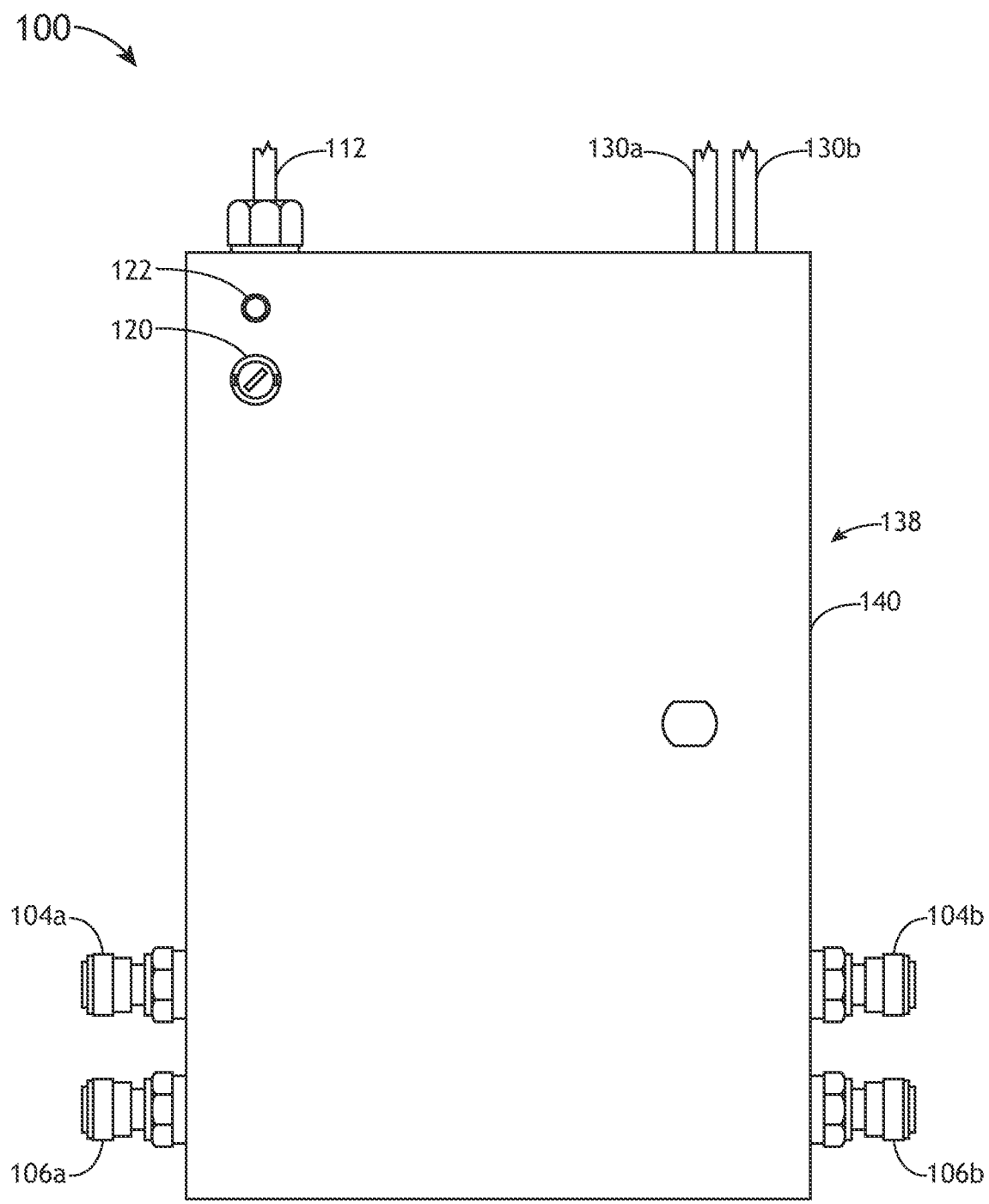
FIG. 1B illustrates a front view of an apparatus for generating aqueous ozone, in accordance with one or more embodiments of the present disclosure.

FIG. 1A illustrates a simplified block diagram of an apparatus 100 for generating aqueous ozone, in accordance with one or more embodiments of the present disclosure. FIGS. 1B-1G generally illustrate the apparatus 100, in accordance of one or more embodiments of the present disclosure. It is noted herein that "apparatus 100" and "ozone generation unit 100" may be considered synonymous for purposes of the present disclosure.

The apparatus 100 may be configurable to a specific design and/or operation dependent on the type and/or amount of aqueous ozone necessary for any particular application, such as a replacement or supplementary component for sanitation devices, laundry machines, wastewater treatment devices, ice makers and other food production devices, or the like.

For example, the apparatus 100 may be configured to generate aqueous ozone to be used for applications including, but not limited to, any sanitation application (e.g., hot water laundry, cold water laundry, janitorial stations, rinse stations, hard surface cleaning, carpet cleaning, floor scrubbing, window washing, personal body washing, pet washing, car washing, or the like). For instance, utilizing the apparatus 100 may substantially reduce (or eliminate) the need for caustic and/or dangerous laundry chemicals, removing the hazard from both users and the environment.

By way of another example, the apparatus 100 may be configured to generate aqueous ozone to be used for applications including, but not limited to, any food preparation application (e.g., making or storing ice; cleaning drinking water; producing soda; brewing coffee, tea, or beer; distilling spirits; cleaning fruits and/or vegetables; boiling food; steaming food; treating well water; or the like). For instance, utilizing the apparatus 100 may negate mold growth in ice makers caused by incorrect ozone concentrations.

By way of another example, the apparatus 100 may be configured to generate aqueous ozone to be used for applications including, but not limited to, any medical application (e.g., fluid sterilization, or the like).

In one embodiment, the apparatus 100 is configured to include one or more production lines. For example, the apparatus 100 may include a first line (e.g., the "a" line including at least components 102a, 104a, 106a, 108a, 124a, 126a, 130a, 132a, 134a, 136a) and at least an additional line (e.g., the "b" line including at least components 102b, 104b, 106b, 108b, 124b, 126b, 130b, 132b, 134b, 136b). It is noted herein that, where the apparatus 100 includes at least two production lines, the at least two production lines are fluidically independent, while sharing one or more integrated circuitry components. For example, the at least two production lines may be independently operated at different times. By way of another example, the at least two production lines may be operated at the same time. However, it is noted herein that the at least two production lines may share one or more fluidic components and one or more integrated circuitry components, where the sharing of the one or more fluidic components does not result in a vacuum forming within the at least two production lines.

In another embodiment, the apparatus 100 includes one or more pipes. For example, the apparatus 100 may include, but is not limited to, a first pipe 102a and at least an additional pipe 102b. The pipes 102a, 102b may be fabricated from any plastic known in the art, any metal known in the art, or the like. For example, the pipes 102a, 102b may be fabricated from a material including, but not limited to, a food-grade plastic, a food-grade metal, or the like. By way of another example, the pipes 102a, 102b may be fabricated from a material including, but not limited to, copper, polyvinyl chloride (PVC), acrylonitrile butadiene styrene (ABS), or the like. In another embodiment, fluid (e.g., municipal water, filtered water, or the like) enters the pipes 102a, 102b through an inlet 104a or 104b, respectively. For example, the inlets 104a, 104b may include, but are not limited to, input hose adapters. In another embodiment, aqueous ozone exits the production lines through an outlet 106a or 106b, respectively. For example, the outlets 106a, 106b may include, but are not limited to, output hose adapters.

In another embodiment, the apparatus 100 includes one or more flow switches, where the one or more flow switches are triggered by fluid flow. For example, the apparatus 100 may include, but is not limited to, a first flow switch 108a and at least an additional flow switch 108b. By way of another example, the flow switches 108a, 108b may include, but are not limited to, one or more electrically-actuated flow switches, one or more analog flow switches, or the like. For instance, the flow switches 108a, 108b may include, but are not limited to, magnetic actuator flow switches, solenoid-driven flow switches, pressure-measuring flow switches, spring-assisted flow switches, pressure-plate flow switches, or the like.

In another embodiment, the flow switches 108a, 108b are coupled to a neutral circuit 110. In another embodiment, the flow switches 108a, 108b are coupled to a power supply via a flow switch terminal 114. For example, the power supply may be a component separate from the apparatus 100, such that only a power cable 112 from the power supply is a component of the apparatus 100. By way of another example, the power supply may be a component of the apparatus 100. For instance, the power supply may be a battery pack, an internal power supply, or the like. In another embodiment, the power cable 112 is coupled to a ground 116. In another embodiment, the power cable 112 is coupled to a power circuit 118 via a fuse terminal 120.

In another embodiment, the power circuit 118 is coupled to the neutral circuit 110 via one or more status indicators 122. For example, the one or more status indicators 122 may include, but are not limited to, an LED light (e.g., single-color or multi-color), a sound emitter, or the like. For instance, the apparatus 100 may include a single status indicator 122 that activates when any production line is in operation. In addition, the apparatus 100 may include a status indicator 122 that activates when a particular production line is in operation. Further, the apparatus 100 may include one or more status indicators 122 configured to indicate a fault in the integrated circuitry (e.g., the neutral circuit 110, the power cable 112, the flow switch terminal 114, the ground 116, the fuse terminal 120, or the like) of the apparatus 100 shared by the production lines.

Figure 1C:
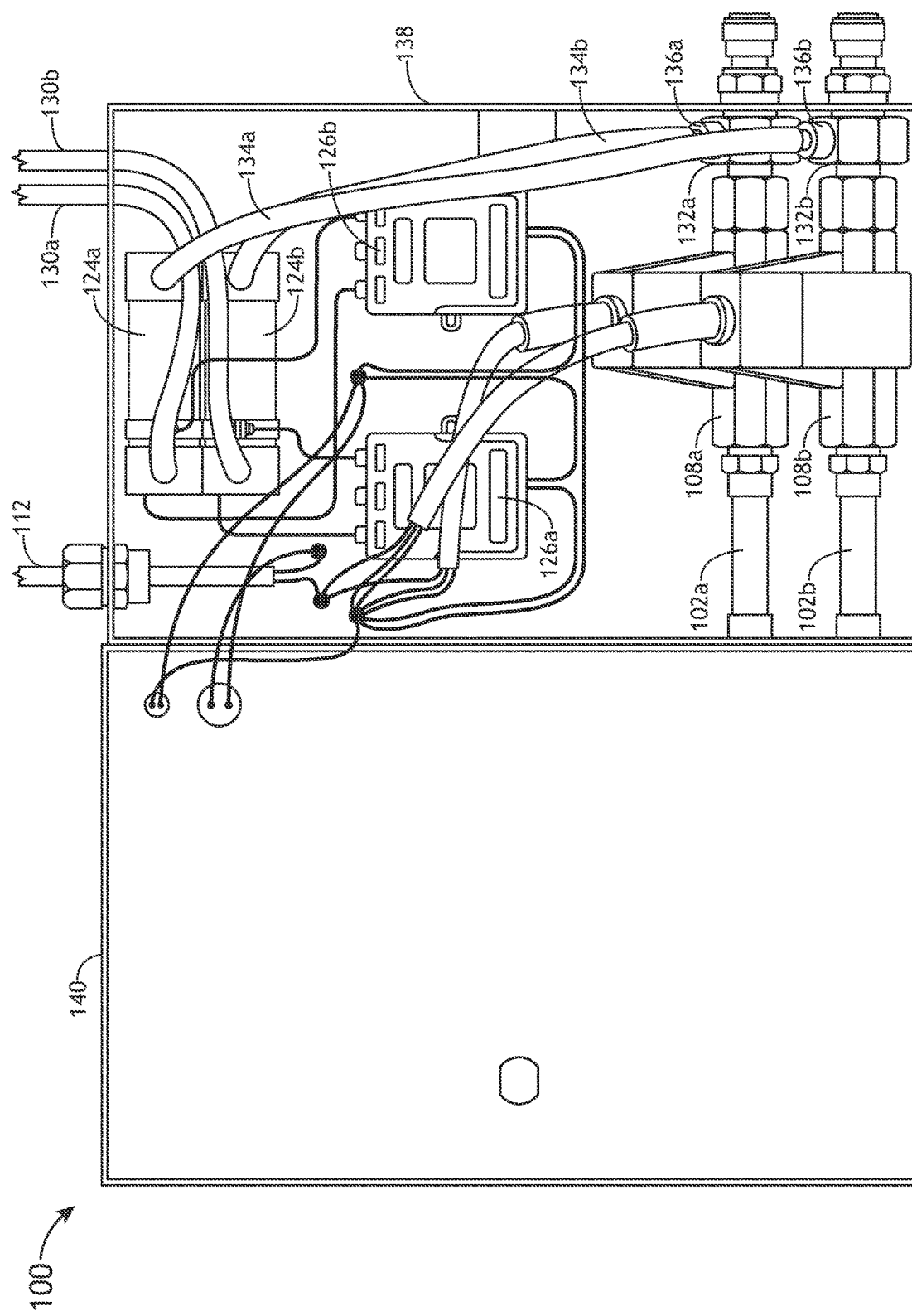
FIG. 1C illustrates a front view of an apparatus for generating aqueous ozone, in accordance with one or more embodiments of the present disclosure.
Figure 1D:
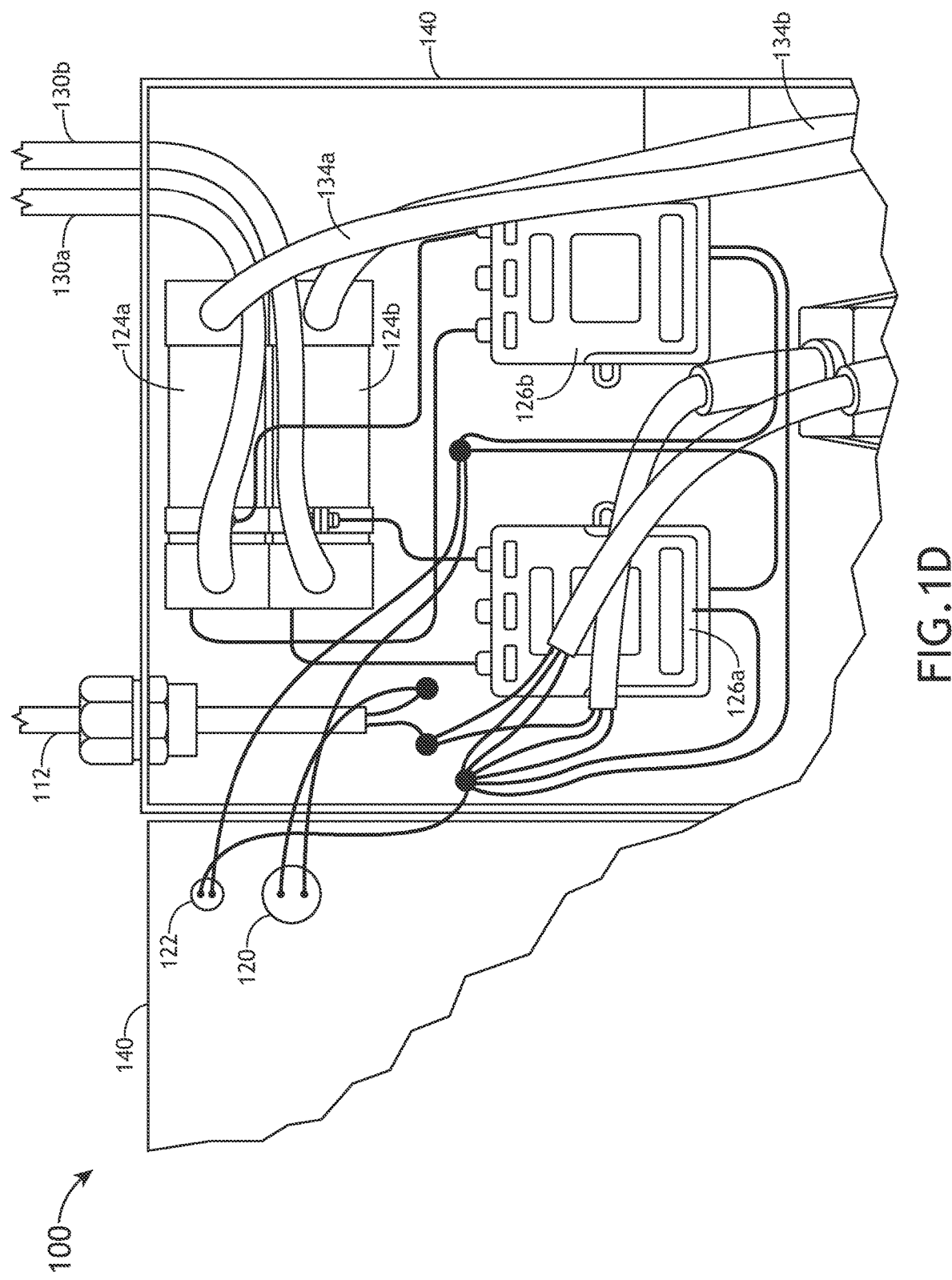
FIG. 1D illustrates a portion of a front view of an apparatus for generating aqueous ozone, in accordance with one or more embodiments of the present disclosure.
Figure 1E:
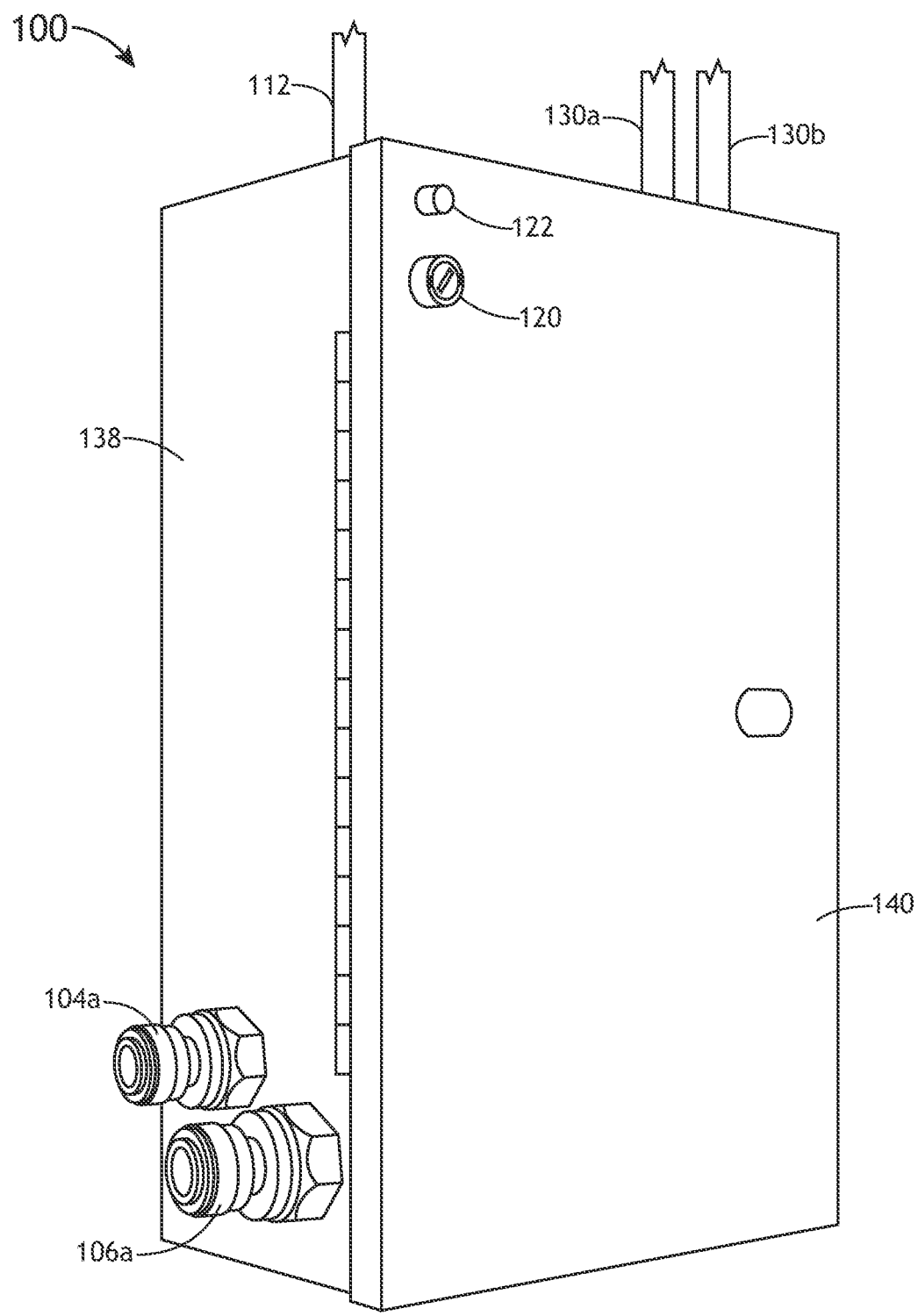
FIG. 1E illustrates a perspective view of an apparatus for generating aqueous ozone, in accordance with one or more embodiments of the present disclosure.
Figure 1F:
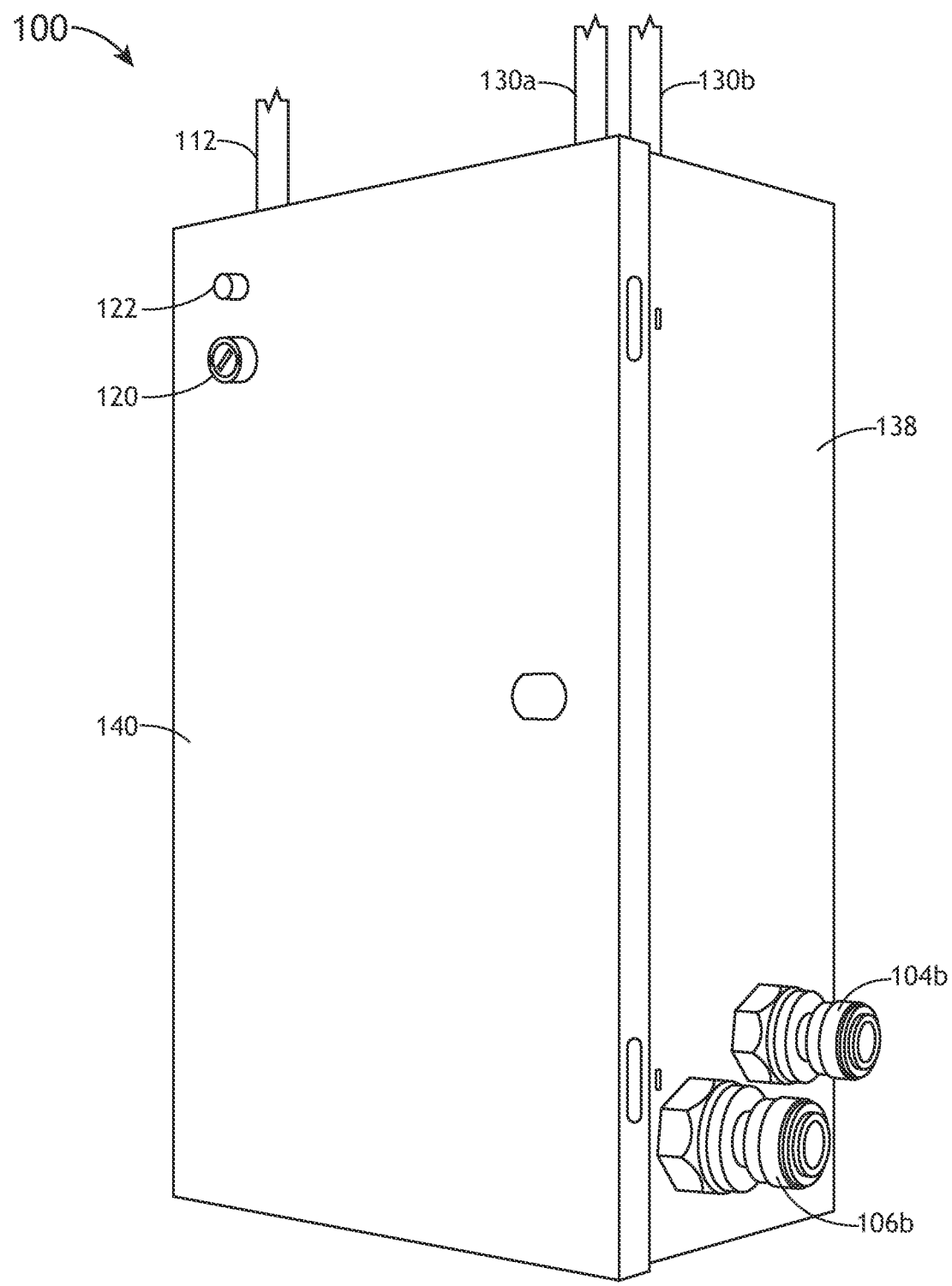
FIG. 1F illustrates a perspective view of an apparatus for generating aqueous ozone, in accordance with one or more embodiments of the present disclosure.
Figure 1G:
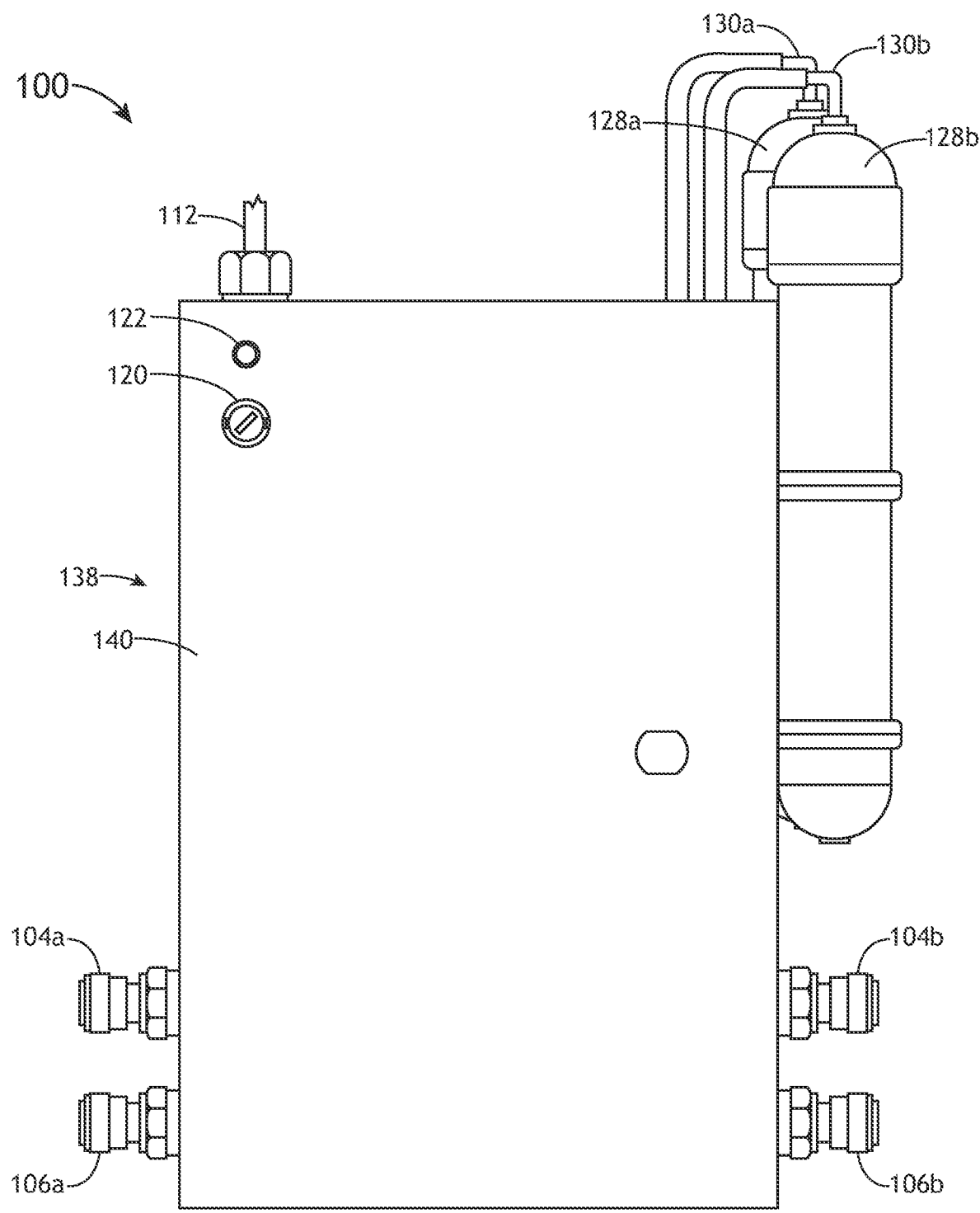
FIG. 1G illustrates a front view of an apparatus for generating aqueous ozone, in accordance with one or more embodiments of the present disclosure.

It is noted herein the nodes shown in FIGS. 1C and 1D are examples of possible points for electrical coupling and/or connection and should not be interpreted as a limitation on the present disclosure but merely an illustration.

In another embodiment, the apparatus 100 includes one or more ozone generators. For example, the apparatus 100 may include, but is not limited to, a first ozone generator 124a and at least an additional ozone generator 124b. By way of another example, the ozone generators 124a, 124b may be driven by alternating current (AC) or direct current (DC) voltage. By way of another example, the ozone generators 124a, 124b may include, but are not limited to, one or more corona-discharge tubes. It is noted herein the ozone generators 124a, 124b may be supplemented and/or replaced by one or more flash reactors.

In another embodiment, the apparatus 100 includes a control component for the ozone generators 124a, 124b. For example, the apparatus 100 may include, but is not limited to a first control component 126a and at least an additional control component 126b. In another embodiment, the control components 126a, 126b are coupled to the neutral circuit 110 and/or the power circuit 118.

In another embodiment, the apparatus 100 includes one or more air dryers. For example, the apparatus 100 may include, but is not limited to, a first air dryer 128a and at least an additional air dryer 128b. By way of another example, the air dryers 128a, 128b may include, but are not limited to, silica gel air dryers. In another embodiment, the ozone generators 124a, 124b are coupled to the air dryers 128a, 128b via an ambient air tube 130a or 130b, respectively. For example, the ambient air tubes 130a, 130b may be fabricated from a material including, but not limited to, silicone. In another embodiment, the air dryers 128a, 128b produce a stable ambient air to ensure selected amounts of ozone are produced within the ozone generators 124a, 124b.

It is noted herein the air dryers 128a, 128b may be a component of the apparatus 100. In addition, it is noted herein the air dryers 128a, 128b are external components coupled to the apparatus 100, such that the apparatus 100 and the air dryers 128a, 128b are components of an encompassing system. Further, it is noted herein the apparatus 100 may receive an air supply from a device other than the air dryers 128a, 128b. Therefore, the above description should not be interpreted as a limitation on the present disclosure but merely an illustration.

In another embodiment, the apparatus 100 includes one or more fittings, where fluid from the flow switches 108a or 108b and ozone from the ozone generators 124a or 124b is mixed within the one or more fittings. For example, the apparatus 100 may include, but is not limited to, a first fitting 132a and at least an additional fitting 132b. By way of another example, the fittings 132a, 132b may include, but are not limited to, tee fittings, wye fittings, or the like. For instance, the fittings 132a, 132b may include, but are not limited to, venturi fittings. For instance, fluid flow rate within each production line may be adjustable prior to the generation of aqueous ozone depending on the dimensions of the fittings 132a, 132b. In another embodiment, the ozone generators 124a, 124b are coupled to the fittings 132a, 132b via a discharge tube 134a or 134b, respectively. For example, the discharge tubes 134a, 134b may be fabricated from a material including, but not limited to, silicone.

In another embodiment, the discharge tubes 134a, 134b are coupled to the fittings 132a, 132b via an adjustable orifice 136a or 136b, respectively. For example, the orifices 136a, 136b may be adjusted to alter the amount of ozone entering the fittings 132a, 132b, subsequently altering the ozone concentration of aqueous ozone generated by the one or more production lines. It is noted herein that generating aqueous ozone at a select concentration via the adjustable orifices 136a, 136b only requires readily-available stoichiometric calculation charts and/or formulas for common inorganic contaminants including, but not limited to, iron, manganese, and sulfide compounds. In this regard, the multiple production lines of the apparatus 100 allow for more efficient on-site and/or on-demand production of aqueous ozone with select properties (e.g., ozone concentration, temperature, or the like).

In one embodiment, as generally illustrated in FIGS. 1B-1G, one or more components of the apparatus 100 are contained within a housing 138. In another embodiment, the housing 138 includes a lid (or cover) 140. For example, the lid 140 may be coupled to the housing 138 via at least one of a hinge, a set of slot-and-groove assemblies, a fastener, a friction latch or clasp, or the like. In another embodiment, one or more components of the apparatus 100 protrude through a surface of the housing 138 (e.g., the power cable 112, the fuse terminal 120, the status indicator 122, or the like). In another embodiment, one or more components of the apparatus 100 are not contained with the housing 138 (e.g., the status indicator 122, the air dryers 128a, 128b, or the like). For example, where the status indicator 122 is an LED light, the status indicator 122 may be wired and positioned a selected distance from the housing 138, such that the status indicator 122 may be visible regardless of the location of the housing 138.

In one embodiment, fluid enters at least one of the pipes 102a, 102b and engages the respective flow switch 108a, 108b. In another embodiment, the engaged flow switch 108a, 108b transmits an electrical signal (e.g., electrical current) to the status indicator 122 via the neutral circuit 110. For example, the electrical signal may be an electrical current of 120V at 60 Hz. In another embodiment, the electrical signal is transmitted to the control components 126a, 126b via the fuse terminal 120 and the power circuit 118. In another embodiment, the control components 126a, 126b cause the respective ozone generators 124a, 124b to generate ozone upon receipt of the electrical signal. In this regard, the flow switches 108a, 108b ensure that any production line (e.g., the first production line "a" or the at least the additional production line "b") of the apparatus 100 is getting a selected concentration of ozone.

In another embodiment, the generated ozone passes through the discharge tubes 134a, 134b and enters the fittings 132a, 132b via the orifices 136a, 136b, respectively. In another embodiment, the generated ozone mixes with the fluid in the pipes 102a, 102b to produce aqueous ozone upon entering the fittings 132a, 132b. It is noted herein that adjusting (e.g., increasing or decreasing) the diameter of the orifices 136a, 136b will increase or decrease the amount of ozone entering the fittings 132a, 132b, resulting in a higher-concentration or lower-concentration aqueous ozone. In this regard, the multiple production lines allow the apparatus 100 to meet Oxidation Reduction Potential (ORP) levels ranging from 650 mV to 800 mV (e.g., levels necessary for cleaning and sanitizing) by changing the size of the orifices 136a, 136b in one or more production lines of the apparatus 100.

It is noted herein that the apparatus 100 is not limited to the above embodiments. In addition, it is noted herein that the apparatus 100 is not limited to the arrangement and/or orientation of components illustrated in the simplified block diagram of FIG. 1A or illustrated in FIGS. 1B-1G. Therefore, the above description should not be interpreted as a limitation on the present disclosure but merely an illustration.

FIGS. 2A-2E generally illustrate a system 200 including the apparatus 100 for generating aqueous ozone, in accordance with one or more embodiments of the present disclosure.

In one embodiment, the system 200 includes one or more fluid sources 202. In another embodiment, the system 200 includes the apparatus 100. In another embodiment, one or more production lines within the apparatus 100 receive fluid from the source 202. For example, the apparatus 100 may include, but is not limited to, a first production line and at least an additional production line. By way of another example, the apparatus 100 may include, but is not limited to, one or more sets of production lines, where each set of production lines includes one or more production lines. In another embodiment, each production line of the apparatus 100 receives fluid from the same fluid source 202. It is noted herein, however, that at least one of the production lines may receive fluid from a first fluid source 202 and at least an additional production line may receive fluid from at least an additional fluid source 202.

Figure 2A:
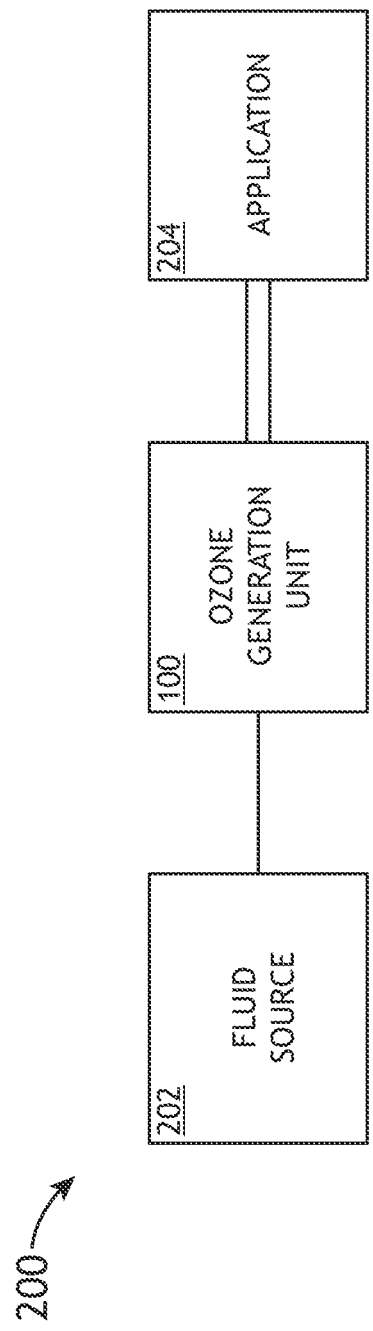
FIG. 2A illustrates a simplified block diagram of a system including an apparatus for generating aqueous ozone, in accordance with one or more embodiments of the present disclosure.

In another embodiment, the system 200 includes one or more applications requiring aqueous ozone. For example, as illustrated in FIG. 2A, the system 200 may include a first application 204, where the one or more production lines of the apparatus 100 generate aqueous ozone tailored to the first application 204. For instance, the apparatus 100 may generate aqueous ozone for the first application 204 including a first temperature and an additional temperature, a first ozone concentration and an additional ozone concentration, or the like via two production lines.

By way of another example, as generally illustrated in FIGS. 2B and 2C, the system 200 may include, but is not limited to, the first application 204 and at least an additional application 206. For instance, as illustrated in FIG. 2B, the first production line of the apparatus 100 generates aqueous ozone tailored to the first application 204 and the at least the additional production line of the apparatus 100 generates aqueous ozone tailored for the at least the additional application 206. In addition, where the apparatus 100 includes at least two sets of production lines and each set of production lines include at least two production lines as illustrated in FIG. 2C, a first set of production lines of the apparatus 100 generates aqueous ozone tailored to the first application 204 and the at least the additional set of production lines of the apparatus 100 generates aqueous ozone tailored for the at least the additional application 206.

Figure 2D:
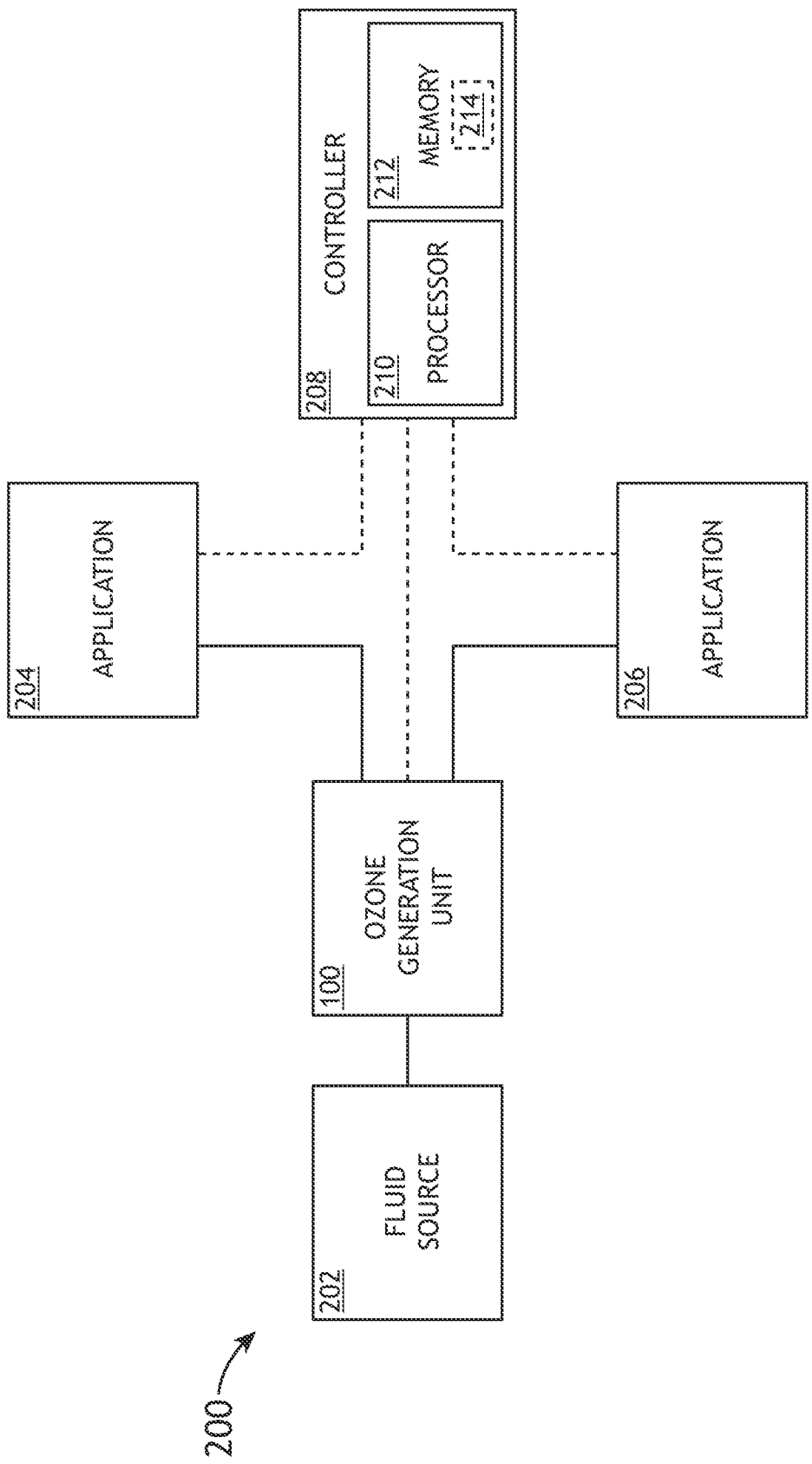
FIG. 2D illustrates a simplified block diagram of a system including an apparatus for generating aqueous ozone, in accordance with one or more embodiments of the present disclosure.

In another embodiment, as illustrated in FIG. 2D, the system 200 includes a controller 208. In another embodiment, the controller 208 is operably coupled to one or more components of the system 200. For example, the controller 208 may be operably coupled to the apparatus 100, the fluid source 202, and/or the applications 204, 206. In this regard, the controller 208 may direct any of the components of the system 200 to carry out any one or more of the various functions described throughout the present disclosure. For example, the controller 208 may control the activation of the ozone generators 124a, 124b, such that apparatus 100 may not include the flow switches 108a, 108b.

In another embodiment, the controller 208 includes one or more processors 210 and memory 212. In another embodiment, the memory 212 stores a set of program instructions 214. In another embodiment, the set of program instructions 214 is configured to cause the one or more processors 210 to carry out any of the one or more process steps described throughout the present disclosure (e.g., one or more steps of method 300).

The controller 208 may be configured to receive and/or acquire data or information from other subsystems or tools of the system 200 (e.g., one or more sets of information from the apparatus 100, the fluid source 202, and/or the applications 204, 206) by a transmission medium that may include wireline and/or wireless portions. In addition, the controller 208 may be configured to transmit data or information (e.g., the output of one or more procedures of the inventive concepts disclosed herein) to one or more subsystems or tools of the system 200 (e.g., one or more sets of information from the apparatus 100, the fluid source 202, and/or the applications 204, 206) by a transmission medium that may include wireline and/or wireless portions. In this regard, the transmission medium may serve as a data link between the controller 208 and the other subsystems of the system 200. In addition, the controller 208 may be configured to send data to external systems via a transmission medium (e.g., network connection).

The one or more processors 210 may include any one or more processing elements known in the art. In this sense, the one or more processors 210 may include any microprocessor device configured to execute algorithms and/or program instructions. For example, the one or more processors 210 may consist of a desktop computer, mainframe computer system, workstation, image computer, parallel processor, handheld computer (e.g., tablet, smartphone, or phablet), or other computer system (e.g., networked computer). In general, the term "processor" may be broadly defined to encompass any device having one or more processing elements, which execute the set of program instructions 214 from a non-transitory memory medium (e.g., the memory 212). Moreover, different subsystems of the system 200 (e.g., one or more sets of information from the apparatus 100, the fluid source 202, and/or the applications 204, 206) may include processor or logic elements suitable for carrying out at least a portion of the steps described throughout the present disclosure (e.g., one or more steps of the method 300). Therefore, the above description should not be interpreted as a limitation on the present disclosure but merely an illustration.

The memory 212 may include any storage medium known in the art suitable for storing the set of program instructions 214 executable by the associated one or more processors 210. For example, the memory 212 may include a non-transitory memory medium. For instance, the memory 212 may include, but is not limited to, a read-only memory (ROM), a random-access memory (RAM), a magnetic or optical memory device (e.g., disk), a magnetic tape, a solid-state drive, and the like. The memory 212 may be configured to provide display information to a display device of a user interface). In addition, the memory 212 may be configured to store user input information from a user input device of the user interface. The memory 212 may be housed in a common controller 208 housing with the one or more processors 210. The memory 212 may, alternatively or in addition, be located remotely with respect to the spatial location of the processors 210 and/or the controller 208. For instance, the one or more processors 210 and/or the controller 208 may access a remote memory 212 (e.g., server), accessible through a network (e.g., internet, intranet, and the like).

In one embodiment, the system 200 includes a user interface. In another embodiment, the user interface is coupled to the controller 208 (e.g., physically coupled, communicatively coupled, or both physically and communicatively coupled). In another embodiment, the user interface includes a display. In another embodiment, the user interface includes a user input device. In another embodiment, the display device is coupled to the user input device. For example, the display device may be coupled to the user input device by a transmission medium that may include wireline and/or wireless portions.

The display device may include any display device known in the art. For example, the display device may include, but is not limited to, a liquid crystal display (LCD). By way of another example, the display device may include, but is not limited to, an organic light-emitting diode (OLED) based display. By way of another example, the display device may include, but is not limited to, a CRT display. Those skilled in the art should recognize that a variety of display devices may be suitable for implementation in the present invention and the particular choice of display device may depend on a variety of factors, including, but not limited to, form factor, cost, and the like. In a general sense, any display device capable of integration with a user input device (e.g., touchscreen, bezel mounted interface, keyboard, mouse, trackpad, and the like) is suitable for implementation in the present invention.

The user input device may include any user input device known in the art. For example, the user input device may include, but is not limited to, a keyboard, a keypad, a touchscreen, a lever, a knob, a scroll wheel, a track ball, a switch, a dial, a sliding bar, a scroll bar, a slide, a handle, a touch pad, a paddle, a steering wheel, a joystick, a bezel input device, or the like. In the case of a touchscreen interface, those skilled in the art should recognize that a large number of touchscreen interfaces may be suitable for implementation in the present invention. For instance, the display device may be integrated with a touchscreen interface, such as, but not limited to, a capacitive touchscreen, a resistive touchscreen, a surface acoustic based touchscreen, an infrared based touchscreen, or the like. In a general sense, any touchscreen interface capable of integration with the display portion of a display device is suitable for implementation in the present invention. In another embodiment, the user input device may include, but is not limited to, a bezel mounted interface.

Figure 2E:
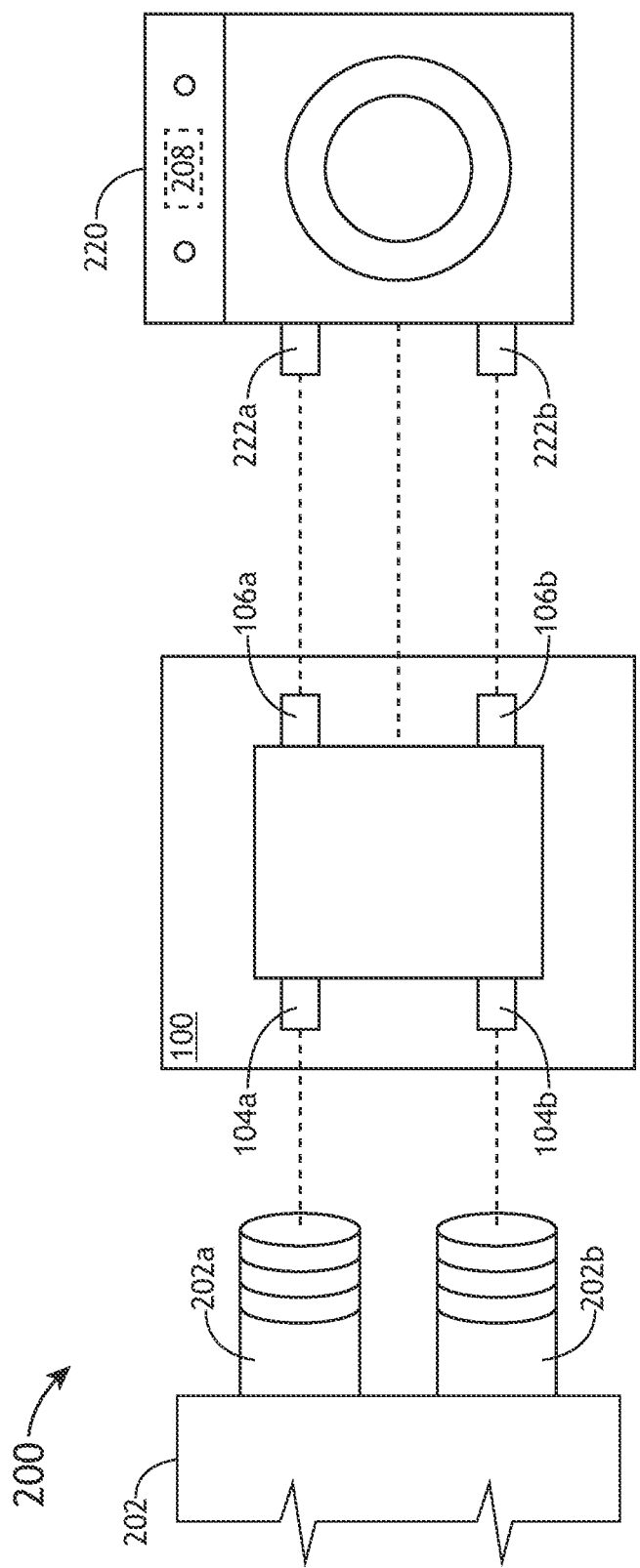
FIG. 2E illustrates a simplified block diagram of a system including an apparatus for generating aqueous ozone, in accordance with one or more embodiments of the present disclosure.

In one embodiment, as illustrated in FIG. 2E, the system 200 includes one or more programmable washing machines 220. In another embodiment, the apparatus 100 receives fluid via the inlets 104a and 104b from outlets 202a, 202b of the fluid source 202. In another embodiment, the one or more programmable washing machines 220 receives aqueous ozone via inlets 222a and 222b from the outlets 106a, 106b of the apparatus 100. For example, the aqueous ozone received may be at a selected temperature (e.g., hot or cold) and/or may be at a selected ozone concentration.

It is noted herein the use of aqueous ozone requires lower fill levels for a given washing machine basin size (e.g., 50% of water volume ranging from 40-100 gallons used in a washing machine basin, or 20-50 gallons) and more rinse/drain cycles (e.g., 5 cycles versus 2 cycles, or any selected number of cycles) than what is required by washing machines using chemicals. In addition, it is noted herein that aqueous ozone works faster and at a stronger cleaning power than other non-chemical oxidizers (e.g., chlorine). However, although embodiments of the present disclosure are directed to utilizing aqueous ozone for applications typically utilizing chemical or non-chemicals such as, but not limited to, laundry, it is noted herein that select fields (e.g., the medical field) require a level of sanitation/sterilization that may only be achieved with the reduced amount of a chemical or non-chemical alternative. Therefore, the above description should not be interpreted as a limitation on the scope of the present disclosure, but merely an illustration.

In another embodiment, the controller 208 is embedded and/or is an integral component of the one or more programmable washing machines 220. For example, the one or more programmable washing machines 220 may control all or part of the system 200, including the one or more programmable washing machines 220, the apparatus 100, and/or the fluid sources 202. It is noted herein, however, that the controller 208 may be separate from the one or more programmable washing machines 220 (e.g., as illustrated in FIG. 2D). Therefore, the above description should not be interpreted as a limitation on the scope of the present disclosure, but merely an illustration.

Figure 3:
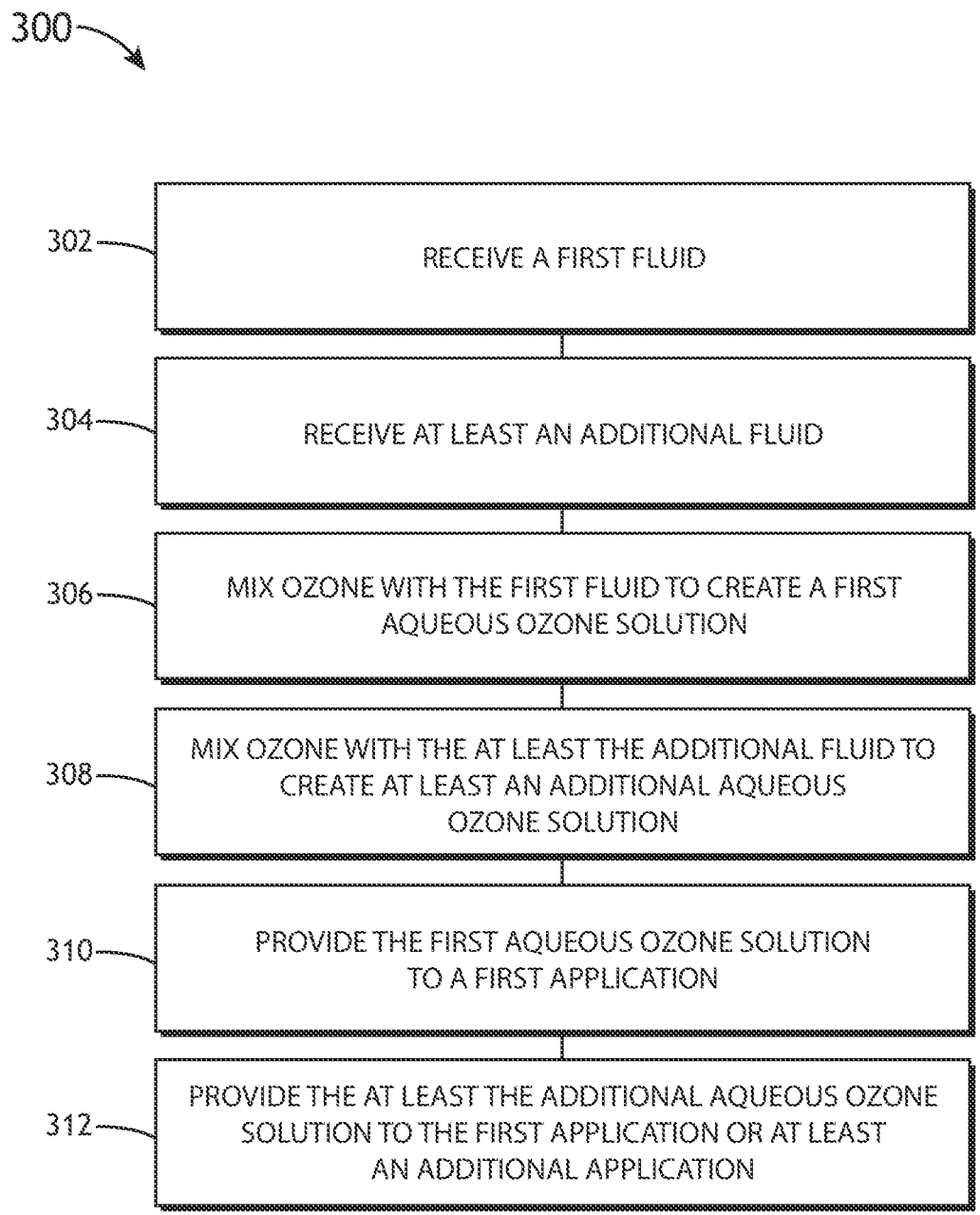
FIG. 3 illustrates a method for generating aqueous ozone via an apparatus for generating the aqueous ozone, in accordance with one or more embodiments of the present disclosure.

FIG. 3 illustrates a method 300 for generating aqueous ozone via the apparatus 100 and/or via the system 200, in accordance with one or more embodiments of the present disclosure. It is noted herein the method 300 is not limited to the steps provided. For example, the method 300 may instead include more or fewer steps. By way of another example, the method 300 may perform the steps in an order other than provided. Therefore, the above description should not be interpreted as a limitation on the scope of the present disclosure, but merely an illustration.

In step 302, a first fluid is received by the apparatus 100. In one embodiment, the first fluid is received from the fluid source 202 by the apparatus 100. In another embodiment, the apparatus 100 includes the first production line. In another embodiment, the first production line receives the first fluid with the pipe 102a via the inlet 104a.

In step 304, at least an additional fluid is received by the apparatus 100. In one embodiment, the at least the additional fluid is received from the same fluid source 202 or a different fluid source 202 by the apparatus 100. In another embodiment, the apparatus 100 includes the at least an additional production line. In another embodiment, the at least the additional production line receives the at least the additional fluid with the pipe 102b via the inlet 104b. It is noted herein that the apparatus 100 may receive the first fluid via the first production line and receive the at least additional fluid via the at least the additional production line either simultaneously, substantially simultaneously, or at separate times.

In step 306, ozone is mixed with the first fluid to generate a first aqueous ozone solution. In one embodiment, the first fluid in the first production line flows through the flow switch 108a and activates the ozone generator 124a to generate ozone. In another embodiment, the generated ozone is mixed with the first fluid within the fitting 132a.

In step 308, ozone is mixed with the at least the additional fluid to generate at least an additional aqueous ozone solution. In one embodiment, the at least the additional fluid in the at least the additional production line flows through the flow switch 108b and activates the ozone generator 124b to generate ozone. In another embodiment, the generated ozone is mixed with the at least the additional fluid within the fitting 132b. It is noted herein that the apparatus 100 may generate the first aqueous ozone solution via the first production line and generate the at least the additional aqueous ozone solution via the at least the additional production line either simultaneously, substantially simultaneously, or at separate times.

In step 310, the first aqueous ozone solution is provided by the apparatus 100 to a first application. In one embodiment, the first aqueous ozone solution exits the first production line of the apparatus 100 via the outlet 106a and is provided to the first application 204.

In step 312, the at least the additional aqueous ozone solution is provided by the apparatus 100 to the first application or at least an additional application. In one embodiment, the at least the additional aqueous ozone solution exits the at least the additional production line of the apparatus 100 via the outlet 106b and is provided to the first application 204. In another embodiment, the at least the additional aqueous ozone solution exits the at least the additional production line of the apparatus 100 via the outlet 106b and is provided to the at least the additional application 206. It is noted herein that the apparatus 100 may provide the first aqueous ozone solution from the first production line to the first application 204 and provide the at least the additional aqueous ozone solution from the at least the additional production line to the first application 204 or the at least the additional application 206 either simultaneously, substantially simultaneously, or at separate times.

Advantages of the present disclosure include an apparatus for generating aqueous ozone. Advantages of the present disclosure also include a system including the apparatus for generating aqueous ozone. Advantages of the present disclosure also include providing the generated aqueous ozone to one or more applications. Advantages of the present disclosure also include a method for generating the aqueous ozone via the apparatus and providing the aqueous ozone to applications.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit device-detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or in addition, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively, or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled/implemented/translated/converted into a high-level descriptor language (e.g., initially implementing described technologies in C, C++, python, Ruby on Rails, Java, PHP, .NET, or Node.js programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors 210 (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.).

Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors 210 such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although a user is described herein as a single figure, those skilled in the art will appreciate that the user may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Although particular embodiments of this invention have been illustrated, it is apparent that various modifications and embodiments of the invention may be made by those skilled in the art without departing from the scope and spirit of the foregoing disclosure. It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Accordingly, the scope of the invention should be limited only by the claims appended hereto.

What is claimed:

1. An apparatus comprising:
    a first production line configured to generate aqueous ozone including a first ozone concentration and an additional production line configured to generate aqueous ozone including an additional ozone concentration, wherein the first production line and the additional production line comprise a flow switch; an ozone generator; and a fitting coupled to the flow switch and the ozone generator,
    wherein the first production line is configured to generate aqueous ozone independently from the additional production line, wherein the ozone concentration of the aqueous ozone contained within and transported by the first production line is different from the ozone concentration of the aqueous ozone contained within and transported by the additional production line, wherein the first production line and the additional production line are coupled to a common electrical system,
    wherein the first production line is configured to couple to a first application; and
    wherein the additional production line is configured to couple to an additional application.

2. The apparatus in claim 1, wherein the first production line and the additional production line comprise:
    an orifice, wherein the ozone generator is coupled to the fitting via the orifice.

3. The apparatus in claim 2, wherein the orifice is adjustable, wherein adjustment of the orifice alters ozone concentration of the aqueous ozone.

4. The apparatus in claim 1, wherein the aqueous ozone generated by the first production line is a different temperature than the aqueous ozone generated by the additional production line.

5. The apparatus in claim 1, wherein the first production line and the additional production line comprise:
    an air dryer coupled to the ozone generator, wherein the air dryer is configured to provide the ozone generator with a stable ambient air.

6. The apparatus in claim 1, wherein the first production line and the additional production line are contained within a common housing.

7. The apparatus in claim 6, wherein the common housing comprises:
    an input hose adapter and an output hose adapter for the first production line, wherein the input hose adapter is configured to provide the first production line with the fluid, wherein the output hose adapter is configured to receive the aqueous ozone generated by the first production line.

8. The apparatus in claim 6, wherein the common housing comprises:
    an input hose adapter and an output hose adapter for the additional production line, wherein the input hose adapter is configured to provide the additional production line with the fluid, wherein the output hose adapter is configured to receive the aqueous ozone generated by the additional production line.

9. The apparatus in claim 1, wherein the common electrical system comprises:
    at least one of a power circuit, a neutral circuit, a flow switch terminal, a fuse terminal, a status indicator, or a power cable.

10. A system, comprising:
    one or more fluid sources;
    a first production line including a first control component coupled to a first ozone generator;
    an additional production line including an additional control component coupled to an additional ozone generator,
        wherein the first production line is configured to generate aqueous ozone independently from the additional production line, wherein the ozone concentration of the aqueous ozone contained within and transported by the first production line is different from the ozone concentration of the aqueous ozone contained within and transported by the additional production line, wherein the first control component and the additional control component are coupled to a neutral circuit and a common power source;
    wherein the first production line is configured to couple to a first application; and
    wherein the additional production line is configured to couple to an additional application.

11. The system in claim 10, wherein the first production line and the additional production line is couplable to an application of the one or more applications.

12. The system in claim 10, further comprising:
    a controller including one or more processors and memory configured to store a set of program instructions, wherein the one or more processors are configured to execute the set of program instructions.

13. A system, comprising:
    one or more fluid sources;
    a first production line including a first control component coupled to a first ozone generator;

an additional production line including an additional control component coupled to an additional ozone generator, wherein the first production line is configured to generate aqueous ozone independently from the additional production line, wherein the ozone concentration of the aqueous ozone contained within and transported by the first production line is different from the ozone concentration of the aqueous ozone contained within and transported by the additional production line, wherein the first control component and the additional control component are coupled to a neutral circuit and a common power source, wherein the first production line and the additional production line are configured to couple to one or more programmable washing machines.

14. The system in claim 13, wherein the aqueous ozone generated by the first production line includes a first temperature, wherein the aqueous ozone generated by the additional production line includes an additional temperature, wherein the first temperature and the additional temperature are different.

15. The system in claim 13, further comprising:

a controller including one or more processors and memory configured to store a set of program instructions, wherein the one or more processors are configured to execute the set of program instructions.

16. The system in claim 15, wherein the controller is a component external to the one or more programmable washing machines.

17. The system in claim 15, wherein the controller is a component integrated into at least one of the one or more programmable washing machines.

* * * * *